US00PP28363P2

(12) United States Plant Patent
Roberts

(10) Patent No.: US PP28,363 P2
(45) Date of Patent: Sep. 5, 2017

(54) MINT PLANT NAMED 'JEFFERSON SPEARMINT'

(50) Latin Name: ***Mentha×gracilis* (syn. *Mentha×gentilis* L.; syn. *Mentha cardiac* (S.F. Gray) Bak.)**
Varietal Denomination: Jefferson Spearmint

(71) Applicant: Essex Laboratories, Inc., Napavine, WA (US)

(72) Inventor: Donald D. Roberts, Independence, OR (US)

(73) Assignee: ESSEX LABORATORIES, INC., Napavine, WA (US)

( * ) Notice: Subject to any disclaimer, the term of this patent is extended or adjusted under 35 U.S.C. 154(b) by 0 days.

(21) Appl. No.: 14/999,750

(22) Filed: Jun. 21, 2016

(51) Int. Cl.
*A01H 5/12* (2006.01)

(52) U.S. Cl.
USPC ..... Plt./259

(58) Field of Classification Search
USPC ..... Plt./259
See application file for complete search history.

(56) References Cited

PUBLICATIONS

Cao, L. and L. Berent, "*Mentha×gracilis* (*arvensis×spicata*) USGS Nonindigenous Aquatic Species Database," Gainesville, FL, and NOAA Great Lakes Aquatic Nonindigenous Species Information System, Ann Arbor, MI. Revision Date Jul. 1, 2014.
Johnson, D. A., "Development of Wilt in Mint in Response to Infection by Two Pathotypes of *Verticillium dahliae* and Co-infection by *Praytylenchus penetrans,*" Plant Disease, 2001, 85(11), pp. 1189-1192.
Lawrence, B. M., "Mint: The Genus *Mentha,*" CRC Press, Boca Raton, FL, 2006, pp. 295-319.
Murray, M. J., "Effect of Plant Maturity on Oil Composition of Several Spearmint Species Grown in Indiana and Michigan," Crop Sci., 1972, 12:723-728.
Tucker, A. O. and D. E. Fairbrother, "The Origin of *Mentha×gracilis* (Lamiaceae). Chromosome Number, Fertility, and Three Morphological Characters," Economic Bot., 1990, 44:183-214.
Zheljazkov, V. D., C. L. Cantrell, T. Astatkie, and M. W. Ebelhar, "Productivity, Oil Content, and Composition of Two Spearmint Species in Mississippi," Agronomy J., 2010, 102(1), pp. 129-133.

*Primary Examiner* — Keith Robinson
(74) *Attorney, Agent, or Firm* — Marger Johnson

(57) ABSTRACT

Mint selection 13-S12-2, denominated 'Jefferson spearmint ' is a new *Mentha* sp. cultivar that produces an essential oil different in composition and has a compact plant type and resistance to mint wilt (*Verticillium dahliae*).

1 Drawing Sheet

Latin name of the genus and species: *Mentha×gracilis* (syn. *Mentha×gentilis* L.; syn. *Mentha cardiac* (S.F. Gray) Bak.).

Variety denomination: 'JEFFERSON SPEARMINT'.

FEDERAL SPONSORSHIP

None

TYPE OF PLANT AND NAME OF VARIETY

The present invention relates to a new and distinct variety of spearmint plant developed from a parent of the species *Mentha×gracilis*. The new variety will be identified as 'Jefferson Spearmint'.

BACKGROUND OF INVENTION

Selection 'Jefferson Spearmint' originated as a seedling from an open pollinated fertile 'Scotch Spearmint' ('Scotch 213', *M.×gracilis*) seedling parent. *Mentha×gracilis*, is a hybrid between *M. spicata* and *M. arvensis*. The fertile spearmint seedling parent to 'Jefferson Spearmint', was one of several mint lines in a polycross breeding system composed of selected male and female fertile genotypes including *M. arvensis* and *M. gracilis.*

DISCOVERY AND ASEXUAL REPRODUCTION

This new mint was developed in a mint breeding program in which the primary objective was to develop a mint variety having a specific oil composition, acceptable yield and resistant to mint diseases. The new variety is resistant to mint wilt (soil-borne fungus *Verticillium dahliae*), but susceptible to mint rust (air-borne fungus *Puccinia menthae*). Selection 'Jefferson Spearmint' has an equivalent oil yield to the control variety *M.×gracilis* in test plots since 2013. This plant was selected from a population of mint seedlings in research plots on land near Monmouth, Oreg., and initially identified as 13-S12-2.

Selection 'Jefferson Spearmint' is asexually propagated to maintain the cultivar's genetic integrity and as a means of increasing the selection for commercial planting. Asexual propagation, by tip cuttings or stolon sections, is a common practice in commercial mint cultivation and serves as a means of propagating the normally sterile mint plant. The inventor has conducted asexual propagation of 'Jefferson Spearmint' for greenhouse and field planting in Monmouth, Oreg., each year since 2013 and the genotype comes true to form with each generation.

SUMMARY OF THE INVENTION

Mint selection 13-S12-2, denominated 'Jefferson Spearmint', is a new *Mentha* sp. cultivar that produces an essential oil different in composition than commercially grown spearmint varieties. The essential oil is similar to standard mint oil in components composition but differs in the typical ratio of components. Organoleptically, it differs from typical *M.×gracilis* spearmint oil. It is more resistant to *Verticillium dahliae* mint wilt than current commercially grown varieties.

BRIEF DESCRIPTION OF THE FIGURES

The accompanying color figure shows typical field grown vegetative growth of 'Jefferson Spearmint' and depicts the color as nearly true as reasonably possible.

FIG. 1 illustrates, in a one year old field grown planting, the flowering pattern and multiple flowering shoots of my new mint plant in accordance with the present invention.

DESCRIPTION OF PLANT

My new mint plant improves upon and is distinct from other mint plants in several characteristics, including but not limited to, the following:

1. The ability to produce an essential oil different in composition but with similar components as 'Scotch Spearmint';
2. A more compact plant but with a branching pattern similar to its parent;
3. A level of resistance to mint wilt (*Verticillium dahliae*) equal to or greater than that of its parent.

The essential oil extracted from 'Jefferson Spearmint' has the same components as that of commercial oil produced by 'Native Spearmint' and 'Scotch Spearmint' as illustrated in Table 1. However, the ratio of oil components differs between the commercial spearmint oil and that of 'Jefferson Spearmint'. The concentration of carvone in the oil of 'Jefferson Spearmint' is lower than that of 'Scotch Spearmint'. The amount of limonene in the oil of 'Jefferson Spearmint' is higher than that of 'Native Spearmint' and 'Scotch Spearmint'. Organoleptically, the oil of 'Jefferson Spearmint' is different from that of 'Scotch Spearmint' or 'Native Spearmint' reflecting the difference in oil component ratios.

TABLE 1

A Composition of 'Jefferson Spearmint' Oil Compared to 'Native' and 'Scotch Spearmint' Oils.

| Essential Oil Components | Commercial 'Native Spearmint' 1/ | Commercial 'Scotch Spearmint' ('Scotch 213') | 2015 Test Plot 'Jefferson Spearmint' 2/ |
|---|---|---|---|
| d-Limonene | 10.5 | 16.8 | 30.3 |
| 1,8-Cineole | 1.4 | 1.3 | <1.0 |
| 3-Octanol | 1.0 | 1.9 | 2.4 |
| Menthone | <1.0 | 1.0 | 1.3 |
| Dihydrocarvone | 1.3 | 0.9 | 3.0 |
| L-carvone | 68.8 | 69.2 | 31.5 |

The numbers listed in the above Table are percentages based upon the analysis of the respective mint oils by gas chromatography. The percentages are determined by calculation of the relative peak areas.
1/ Commercial oil sample typical of what is produced by mint growers.
2/ 'Jefferson Spearmint' oil distilled from plants grown in test plots near Madras, Oregon, in 2015.

The numbers listed in the above Table are percentages based upon the analysis of the respective mint oils by gas chromatography. The percentages are determined by calculation of the relative peak areas.

1/ Commercial oil sample typical of what is produced by mint growers.

2/ 'Jefferson Spearmint' oil distilled from plants grown in test plots near Madras, Oreg., in 2015.

TAXONOMIC DESCRIPTION OF 'JEFFERSON SPEARMINT'

This new mint plant, under greenhouse and field growing conditions, is a bush type plant with lateral branches at each node of the main stems. The height of 'Jefferson Spearmint' is slightly less than 'Native Spearmint' growing under similar conditions and will vary based on fertilizer, soil quality, and water application, amongst other known factors that affect growth patterns. 'Jefferson Spearmint' is between 0.3 and 0.5 m at mid-stem in width and 0.9 to 1.2 m in height under greenhouse environment. Field grown 'Jefferson Spearmint' has a width of 0.3 to 0.5 m and a height of 0.8 to 1.2 m. Secondary and tertiary branching occurs to form a compact growth habit. When 'Jefferson Spearmint' is mature and ready for harvest, the main stem at mid-plant (approximately between the eleventh and twelfth node) is 4.9-7.9 mm in width. The secondary and tertiary branch stems are 2.5-2.7 mm and 1.2 mm in width, respectively. The stems are square, glabrous, and a green color that matches The Fifth Edition Royal Horticultural Society Colour Chart 138A green group.

Mature leaves on 'Jefferson Spearmint' are ovate with an acute tip and rounded base. The adaxial leaf surface is sparsely hairy. The abaxial leaf surface is sub-glabrous with oil glands distributed across the surface. Mid-main stem leaf size at flowering is 27-31 mm in width and 49-53 mm in length. Leaf size on secondary branches at flowering is 17-21 mm in width and 31-39 mm in length. Leaf petioles on the main stem leaves are 4.3-7.1 mm in length while petioles on secondary branch stem leaves are 1.6 mm in length. Leaves on the mid-main stem are dentate. The main stem leaves are toothed having from 8-9 teeth on each side. Secondary branch leaves have 2 teeth on each side. The abaxial leaf is dark green in color, ranging from The Fifth Edition Royal Horticultural Society Colour Chart 138A in the green group classification. The leaf has 6-8 lateral veins, more or less in parallel off the main vein that runs from the petiole to the tip of the leaf. The veins are prominent in all leaves of 'Jefferson Mint Spearmint'.

The inflorescence is a cylindrical spike with capitate flowers developing at the nodes of the stem. The capitate flowers are 12-13 mm in width and 6 mm in length. The flowers consist of five petals fused into a two lipped corolla. The corolla is light in color as illustrated in The Fifth Edition Royal Horticultural Society Colour Chart NN155D in the white group. The calyx is generally yellow-green and is 143A of The Fifth Edition Royal Horticultural Society Colour Chart, green group. The gynoecium consists of a single pistil with two lobed stigma that is exserted. The androecium consists of four stamens, each with a distinct filament and anther. Under field conditions, the plant begins flowering in late June to early July.

'Jefferson Spearmint' is both female and male fertile and sheds moderate amount of pollen at maturity. Seed color ranges in color that matches The Fifth Edition Royal Horticultural Society Colour Chart brown group 200A to 200B. Seed are oval shaped with a width of 0.4 mm to 0.5 mm and a length of 0.6 mm to 0.8 mm.

While the plant that comprises the present invention has been described in connection with a specific embodiment thereof, it will be understood that this application is intended to cover any variation, uses, or adaptation of the invention (particular those induced by cultivation under different environmental conditions) following, in general, the principles of the invention and including such departures from the present disclosures as come within known or customary practice in the art to which the invention pertains and as may be applied to the essential features hereinbefore set forth, and as fall within the scope of the invention and the limits of the appended claim.

I claim:

1. A new and distinct variety of spearmint plant, substantially as shown and described, characterized particularly by improving resistance to mint wilt, and producing a unique essential oil.

* * * * *

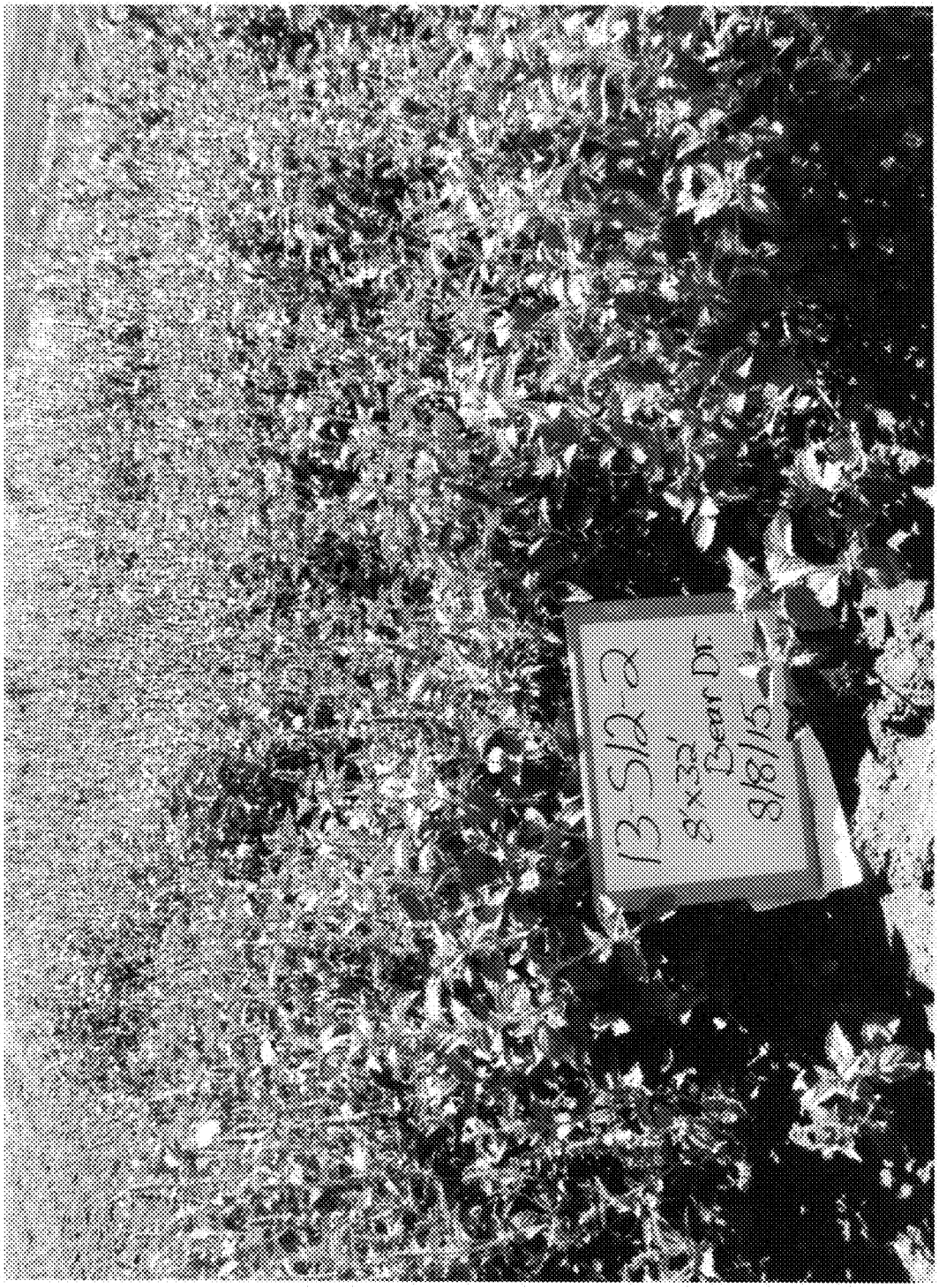
12 SPQ
8/8/15